United States Patent
Yakubovsky et al.

(10) Patent No.: US 7,412,027 B2
(45) Date of Patent: Aug. 12, 2008

(54) METHODS AND SYSTEM FOR MULTI-MODALITY IMAGING

(75) Inventors: Leonid Yakubovsky, Kiriat Bialik (IL); Hernan Altman, Nesher (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 151 days.

(21) Appl. No.: 10/755,804

(22) Filed: Jan. 12, 2004

(65) Prior Publication Data

US 2005/0152492 A1 Jul. 14, 2005

(51) Int. Cl.
*G01N 23/04* (2006.01)
*H05G 1/02* (2006.01)

(52) U.S. Cl. .................. 378/63; 378/195; 378/196
(58) Field of Classification Search .......... 378/20, 378/63, 195, 196
See application file for complete search history.

(56) References Cited

U.S. PATENT DOCUMENTS

| | | | | |
|---|---|---|---|---|
| 5,259,011 A | * | 11/1993 | Petro | 378/4 |
| 5,391,877 A | | 2/1995 | Marks | |
| 5,615,430 A | * | 4/1997 | Nambu et al. | 5/600 |
| 5,851,182 A | * | 12/1998 | Sahadevan | 600/407 |
| 6,045,262 A | * | 4/2000 | Igeta et al. | 378/209 |
| 6,094,760 A | * | 8/2000 | Nonaka et al. | 5/601 |
| 6,205,347 B1 | * | 3/2001 | Morgan et al. | 600/407 |
| 6,302,579 B1 | * | 10/2001 | Meyer et al. | 378/196 |
| 6,385,480 B1 | * | 5/2002 | Bachus et al. | 600/411 |
| 6,435,713 B1 | * | 8/2002 | Iizuka | 378/195 |
| 6,490,476 B1 | | 12/2002 | Townsend et al. | |
| 6,631,284 B2 | | 10/2003 | Nutt et al. | |
| 6,640,364 B1 | * | 11/2003 | Josephson et al. | 5/601 |
| 6,857,778 B2 | * | 2/2005 | Mun et al. | 378/206 |
| 6,917,666 B2 | * | 7/2005 | Wollenweber | 378/20 |
| 6,928,142 B2 | * | 8/2005 | Shao et al. | 378/63 |
| 2004/0057557 A1 | * | 3/2004 | Nafstadius | 378/209 |
| 2006/0036160 A1 | * | 2/2006 | Altman et al. | 600/415 |

FOREIGN PATENT DOCUMENTS

JP 05344964 A * 12/1993

* cited by examiner

*Primary Examiner*—Edward J. Glick
*Assistant Examiner*—Thomas R Artman
(74) *Attorney, Agent, or Firm*—The Small Patent Law Group LLP; Dean D. Small

(57) ABSTRACT

A method of examining a patient is provided. The method includes aligning a patient table with a first examination axis, imaging a patient utilizing a first imaging modality while the patient is oriented along the first examination axis, aligning a patient table with a second examination axis, the second examination axis being different than the first examination axis, and imaging a patient utilizing a second separate imaging modality while the patient is oriented along the second examination axis.

16 Claims, 2 Drawing Sheets

METHODS AND SYSTEM FOR MULTI-MODALITY IMAGING

BACKGROUND OF THE INVENTION

This invention relates generally to imaging systems capable of operation in multiple modalities, and more particularly to methods and systems for maintaining an alignment of the object being scanned.

Multi-modality imaging systems are capable of scanning using different modalities, such as, for example, Positron Emission Tomography (PET), Single Positron emission tomography (SPECT), Ultrasound, Magnetic Resonance Imaging (MRI), and Computed Tomography (CT), Static X-Ray imaging, and Dynamic (Fluoroscopy) X-Ray imaging. In a multi-modal system (also referred to as a multi-modality system), a portion of the same hardware is utilized to perform different scans (e.g., an image produced by SPECT is processed and displayed respectively, by the same computer and display, as an image produced by CT). However, the data acquisition systems (also referred to as an "imaging assembly") are different. For example, on a CT/SPECT system, a radiation source and a radiation detector are used in combination to acquire CT data, while a radiopharmaceutical is typically employed in combination with a SPECT camera to acquire SPECT data.

In multi-modality systems, such as, for example, an integrated SPECT/CT system there is an inherent registration of the SPECT and CT images the system acquires. Since the patient lies still on the same table during the SPECT and CT portions of the acquisition, the patient will be in a consistent position and orientation during the two acquisitions, greatly simplifying the process of correlating and fusing the CT and SPECT images. This allows the CT image to be used to provide attenuation correction information for the reconstruction of the SPECT image, and allows an image reader to easily correlate the anatomic information presented in the CT image and the functional information presented in the SPECT image.

This inherent registration assumes an alignment of the SPECT and CT detector coordinate systems, or at least a known spatial transformation between the two coordinate systems. A misalignment of the coordinate systems may directly result in a misregistration of the images. Misregistration leads not only to wrong localization but also to wrong attenuation correction of the functional image.

Proper SPECT and CT image registration also requires an alignment of the axial (z-) axis of the SPECT and CT coordinate systems not only with each other, but also with the travel axis of the table that transports the patient between and during the SPECT and CT acquisitions. A co-axial SPECT/CT or other multi-modality system, especially for whole body scans, requires a relatively long axial travel distance to permit both imaging modalities the ability to image the region of interest. However, a patient table and table support may not be able to accommodate the alignment requirements while supporting a patient cantilevered out from the table support during an examination due to the extreme length of travel the patient table must travel to reach both imaging assemblies. For example, a co-axial imaging assembly arrangement requires a relatively long rail system, and the length of the bed may induce bending thereof, such that the patient position may change between the two imaging stations, even if the patient remains absolutely stationary.

BRIEF DESCRIPTION OF THE INVENTION

In one embodiment, a method of examining a patient is provided. The method includes aligning a patient table with a first examination axis, imaging a patient utilizing a first imaging modality while the patient is oriented along the first examination axis, aligning a patient table with a second examination axis, the second examination axis being different than the first examination axis, and imaging a patient utilizing a second separate imaging modality while the patient is oriented along the second examination axis.

In another embodiment, an imaging system is provided. The imaging system includes at least a first and a second separate imaging assembly for obtaining medical diagnostic images of a patient for at least first and second imaging modalities wherein the imaging assemblies are aligned along different first and second examination axes, a table configured to hold a patient during the first and the second examination, and a support mechanism moving at least one of the first imaging assembly, the second imaging assembly, and the table between a first and a second examination position aligned with the first and second examination axes for corresponding first and second imaging assemblies.

DETAILED DESCRIPTION OF THE INVENTION

Figure 1:
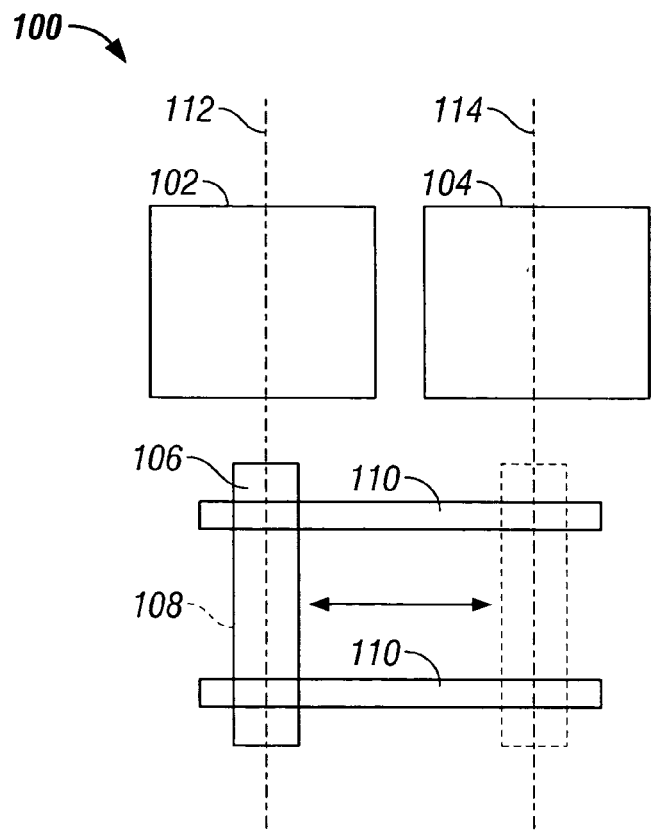
FIG. 1 is a schematic illustration of an imaging system in accordance with an exemplary embodiment of the present invention.

FIG. 1 is a schematic illustration of an exemplary embodiment of an imaging system 100. Imaging system 100 includes a first imaging assembly 102, a second imaging assembly 104, a patient table 106, and a support mechanism 108. In the exemplary embodiment, support mechanism 108 includes at least one guide member 110, such as, but, not limited to, a track or rail. Imaging assembly 102 includes an associated examination axis 112, and imaging assembly 104 includes an associated examination axis 114. As used herein, each examination axis is referenced to a respective imaging apparatus being used to image the patient. In an alternative embodiment, guide member 110 may include a transport mechanism, such as, but not limited to, an air cushion, rollers, and casters, that permits unguided movement from examination axis 112 to examination axis 114, and includes an anchoring mechanism (not shown) to fix support mechanism 108 aligned along examination axis 112 and/or aligned along examination axis 114. At least one anchor dock may be fixed to a base (not shown), such as an examination room floor.

Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly. Imaging assemblies 102 and 104 are oriented side-by-side such that examination axes 112 and 114 are substantially parallel.

In operation, a patient (not shown) may lie supine upon table 106 and aligned along examination axis 112. Support mechanism 108 is used to extend patient table 106 and, for example, the patient into imaging assembly 102 along examination axis 112 to perform a first imaging scan. Support mechanism 108 is used to retract the patient table and the patient to a predetermined stable position of support mechanism 108 and patient table 106. Support mechanism 108 is then used to move patient table 106 laterally such that patient table 106 is aligned with examination axis 114. Support mechanism 108 is used to extend patient table 106 and the patient into imaging assembly 104 along examination axis 114 to perform a second imaging scan, and to retract the patient table and the patient to a predetermined stable position of support mechanism 108 and patient table 106. To facilitate maintaining alignment of the patient, patient table 106 and each examination axis 112 and 114 during lateral translation of support mechanism 108, one or more guide members 110 may be securely coupled to the base, relative to imaging assemblies 102 and 104. In the alternative embodiment, after imaging the patient by imaging assembly 102, table 106 is un-anchored from a position in alignment with examination axis 112, moved to a position in alignment with examination axis 114, and table 106 is then anchored in position. In such embodiment, imaging assembly 102 may be located remotely from imaging assembly 104, for example, in a different examination room.

System 100 may be calibrated for systemic and non-systemic misregistration. In the exemplary embodiment, system 100 is calibrated using a fiduciary marked phantom (not shown) positioned in a predetermined location on patient table 106, which is extended into a predetermined imaging position in first imaging assembly 102, such that a first imaging modality image is generated. Patient table 106 is retracted, moved along guide members 110 to examination axis 114, extended into imaging assembly 104, and a second imaging modality image is generated. The two images may be compared directly, and because it is known that the phantom did not move between the two imaging processes, this comparison enables correction data to be generated which can be used to calibrate the position and magnification of imaging assemblies 102 and 104 relative to the positions of patient table 106, such that their images produced refer to the same position of patient table 106. In the exemplary embodiment, the correction data is used to physically adjust the position of table 106 relative to one or both of imaging assemblies 102 and 104, or vice versa, such as by means of adjustment screws (not shown). In an alternative embodiment, no physical adjustment of the misalignment is performed, but the correction data is used to generate data for applying to one or both sets of the resulting images thereafter, to correct the now known misalignments. In another alternative embodiment, the correction data is used to physically adjust the position of table 106 relative to one or both of imaging assemblies 102 and 104, or vice versa, such as by means of adjustment screws (not shown) to account for a gross misalignment, and a fine adjustment is applied to one or both sets of the resulting images thereafter, to correct the now known misalignments. Once the pre-calibration has been performed by any of these exemplary methods, when used on patients, all of the imaging systems can then refer directly to the image details as if on an equivalently localized table, because the correlation between the table localization in the two systems is accurately known. In an alternative embodiment, the fiduciary marked phantom may be integrated into the patient table. For example, a plurality of indentations or holes may be formed in a surface of patient table 106 wherein the first modality, such as the CT imaging modality, is capable of viewing the indentations or holes. One or more radioactive sources may be positioned within the indentations or holes such that the one or more radioactive sources is capable of being imaged by a second imaging modality, such as, a SPECT or PET imaging modality.

Non-systemic may be affected by factors that may change between each image acquisition, for example, patient dependent factors such as patient weight and patient position on table 106. Differential non-systemic misregistration may be facilitated being reduced by maintaining substantially identical conditions of table 106 and support mechanism 108 between scans, such that the non-systemic misregistration for both imaging modalities may be ignored. Such substantially identical conditions of table 106 and support mechanism 108 between scans may be attained by mounting imaging assemblies 102 and 104 such that a distance from table 106 and support 108 to an imaging scan plane of each imaging assembly 102 and 104 is substantially identical for both imaging assemblies 102 and 104.

Figure 2:
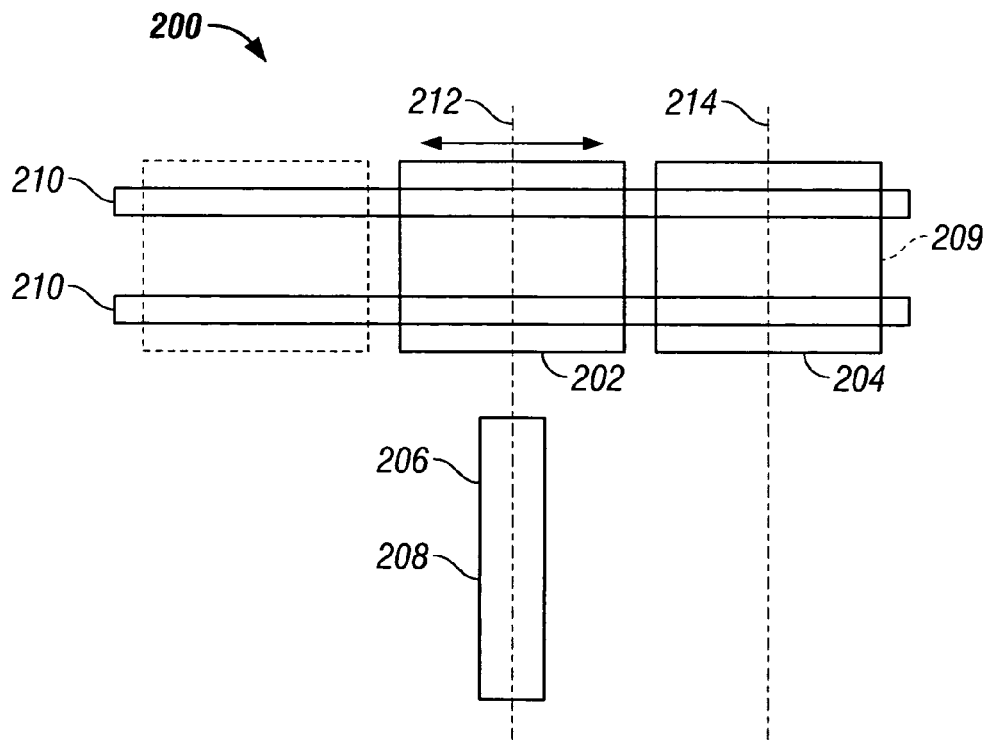
FIG. 2 is a schematic illustration of an exemplary embodiment of another imaging system.

FIG. 2 is a schematic illustration of an exemplary embodiment of an imaging system 200. Imaging system 200 includes a first movable imaging assembly 202, a second movable imaging assembly 204, a patient table 206, and a stationary support mechanism 208. In the exemplary embodiment, a laterally translatable trolley 209 includes at least one guide member 210, such as, but, not limited to, a track or rail. Imaging assembly 202 includes an associated examination axis 212, and imaging assembly 204 includes an associated examination axis 214. As used herein, each examination axis is referenced to a respective imaging apparatus being used to image the patient. When patient table 206 remains stationary and imaging assemblies 202 and 204 are moved laterally, an associated examination axis 212 or 214 is moved laterally with the imaging assembly. Trolley 209 may include a transport mechanism, such as, but not limited to, an air cushion, rollers, and casters, that permits unguided movement from examination axis 212 to examination axis 214, and includes a fastener (not shown) to fix trolley 209 aligned along examination axis 212 and/or aligned along examination axis 214.

Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly. Imaging assemblies 202 and 204 are oriented side-by-side such that examination axes 212 and 214 are substantially parallel.

In operation, a patient (not shown) may lie supine upon table 206 and a position of imaging assembly 202 adjusted such that the patient is aligned along examination axis 212. Support mechanism 208 is used to extend patient table 206 and the patient into imaging assembly 202 along examination axis 212 to perform a first imaging scan. Support mechanism 208 is used to retract patient table 206 and the patient to a predetermined stable position of support mechanism 208 and patient table 206. Trolley 209 is then used to move imaging assemblies 202 and 204, either separately, or in combination, such that patient table 206 is aligned with examination axis 214. Support mechanism 208 is used to extend patient table 206 and the patient into imaging assembly 204 along examination axis 214 to perform a second imaging scan, and to retract patient table 206 and the patient to a predetermined stable position of support mechanism 208 and patient table 206. To facilitate maintaining alignment of the patient, patient table 206 and each examination axis 212 and 214 during lateral translation of trolley 209, one or more guide members 210 may be securely coupled to a base (not shown), such as, a floor, relative to patient table 206. In the alternative embodiment, after imaging the patient by imaging assembly 102, imaging assembly 202 is un-anchored from a position wherein table 206 is in alignment with examination axis 212, imaging assembly 202 is moved, sequentially or simultaneously with imaging assembly 204, to a position wherein table 206 is in alignment with examination axis 214, and imaging assembly 204 is then anchored in position.

Figure 3:
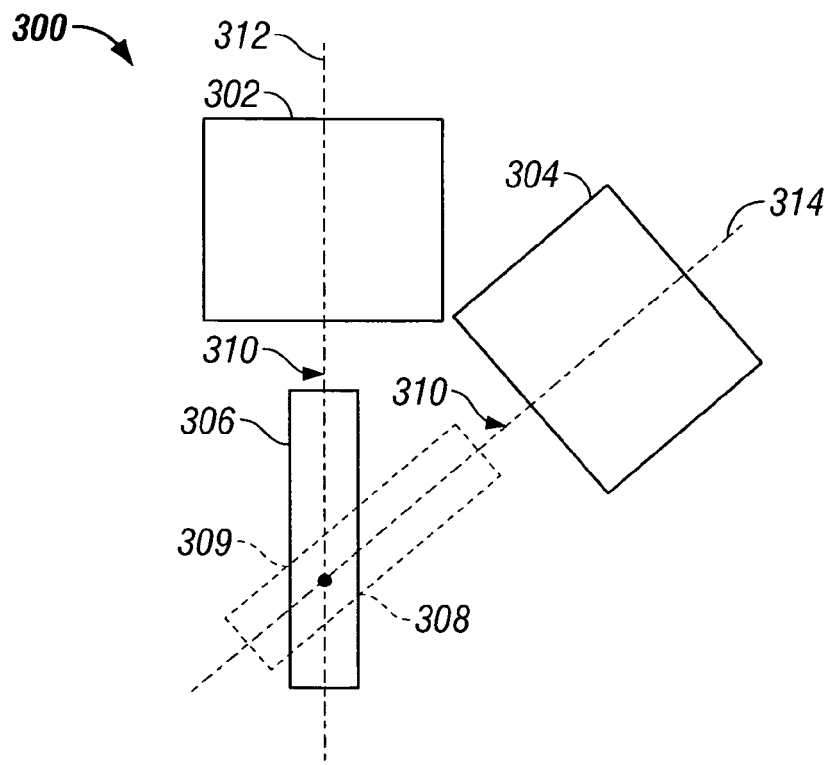
FIG. 3 is a schematic illustration of an exemplary embodiment of another imaging system.

FIG. 3 is a schematic illustration of an exemplary embodiment of an imaging system 300. Imaging system 300 includes a first imaging assembly 302, a second imaging assembly 304, a patient table 306, and a support mechanism 308. Each of imaging assemblies are configured to be fixedly mounted in fixed relation to support mechanism 308, which is stationary and pivotable about a center post member 309, such as a bearing. Support mechanism 308 may be configured to pivot only through a predetermined angle 310, which may be determined, for example, based upon the configuration of center post member 309, or upon a user input. Alternatively, support mechanism 308 may be configured to pivot through an angle greater than angle 310. Angle 310 may be variably selectable based on a size and/or configuration of an examination room containing at least a portion of system 100. Imaging assembly 302 includes an associated examination axis 312, and imaging assembly 304 includes an associated examination axis 314. As used herein, each examination axis is referenced to a respective imaging apparatus being used to image the patient.

Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly. Imaging assemblies 302 and 304 may be oriented at a predetermined angle 310 with respect to each other.

In operation, a patient (not shown) may lie supine upon table 306 and a position of support mechanism 308 adjusted such that the patient is aligned along examination axis 312. Support mechanism 308 is used to extend patient table 306 and the patient into imaging assembly 302 along examination axis 312 to perform a first imaging scan. Support mechanism 308 is used to retract patient table 306 and the patient to a predetermined stable position of support mechanism 308 and patient table 306. Patient table 306 is aligned with examination axis 314 using support mechanism 308 to rotate patient table 306 through angle 310. Support mechanism 308 is used to extend patient table 306 and the patient into imaging assembly 304 along examination axis 314 to perform a second imaging scan, and to retract patient table 306 and the patient to a predetermined stable position of support mechanism 308 and patient table 306.

Figure 4:
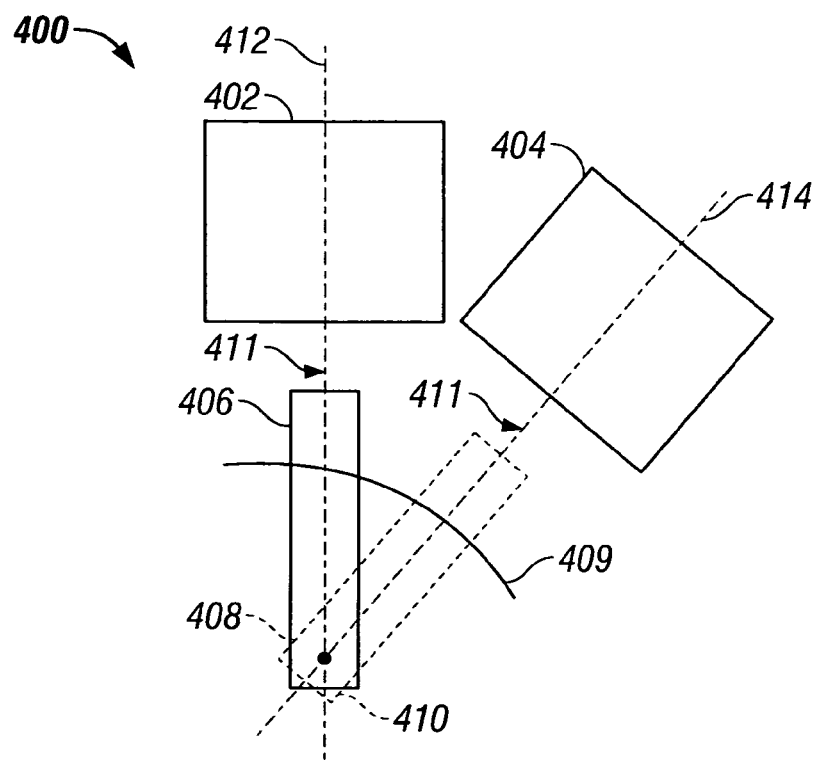
FIG. 4 is a schematic illustration of an exemplary embodiment of another imaging system.

FIG. 4 is a schematic illustration of an exemplary embodiment of an imaging system 400. Imaging system 400 includes a first imaging assembly 402, a second imaging assembly 404, a patient table 406, and a stationary support mechanism 408. In the exemplary embodiment, support mechanism 408 includes at least one guide member 409, such as, but, not limited to, a track or rail. Each of imaging assemblies 402 and 404 are configured to be fixedly mounted in fixed relation to support mechanism 408, which is stationary and pivotable about a distal end member 410, such as a bearing. Support mechanism 408 may be configured to pivot only through a predetermined angle 411, which may be determined, for example, based upon the configuration of distal end member 410, or upon a user input. Alternatively, support mechanism 408 may be configured to pivot through an angle greater than angle 411. Imaging assembly 402 includes an associated examination axis 412, and imaging assembly 404 includes an associated examination axis 414. As used herein, each examination axis is referenced to a respective imaging apparatus being used to image the patient. In the exemplary embodiment, support mechanism 408 includes at least one guide member 409, such as, but, not limited to, a track or rail.

Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly.

In operation, a patient (not shown) may lie supine upon table 406 and a position of support mechanism 408 adjusted such that the patient is aligned along examination axis 412. Support mechanism 408 is used to extend patient table 406 and the patient into imaging assembly 402 along examination axis 412 to perform a first imaging scan. Support mechanism 408 is used to retract patient table 406 and the patient to a predetermined stable position of support mechanism 408 and patient table 406. Patient table 406 is aligned with examination axis 414 using support mechanism 408 to rotate patient table 406 through angle 411. Support mechanism 408 is used to extend patient table 406 and the patient into imaging assembly 404 along examination axis 414 to perform a second imaging scan, and to retract patient table 406 and the patient to a predetermined stable position of support mechanism 408 and patient table 406.

Each of the above described systems may be calibrated similarly to the method described relative to imaging system 100. Each imaging assembly may be configured to movement relative to each other, the patient table, examination room contents, and examination room structure to facilitate removal of imaging assembly covers for maintenance access to internal components.

It is contemplated that the benefits of the invention accrue to all multi-modality imaging systems, such as, for example, but not limited to, a CT/SPECT imaging system as well as systems utilizing currently unknown modalities as well as combinations, such as, for example, but not limited to, a combination SPECT/ultrasound system and/or a CT/MRI system.

The above-described multi-modality imaging systems provide a cost-effective and reliable means for examining a patient. More specifically, each imaging system includes configuration components that may be chosen to satisfy a particular imaging requirements, such as, but not limited to, size of an examination room, shape of an examination room, and component location limitations, such as a floor load limit. For example, a co-axial system may require a relatively larger room size due to "dead space" between the first imaging modality scan plane and the second imaging modality scan plane in the co-axial configuration. As a result, an imaging system is provided that permits multi-modality imaging while maintaining flexibility in cost and available floor space constraints. Further benefits of the described embodiments include facilitating maintenance and operation access to the imaging assemblies, reducing movable structure when moving the relatively lighter table versus the heavier imaging assemblies, and reducing cost through use of relatively less expensive rotational motion relative to translational motion. Furthermore, other modalities may be combined, in a multi-modality system, with a MRI modality without the other modalities being adversely affected by stray magnetic fields form the MRI modality. In a co-axially aligned multi-modality system, modalities that are sensitive to magnetic fields, for example, modalities that have photomultiplier tubes, such as nuclear medicine and CT modalities, may not be able to be economically combined.

An exemplary embodiment of a multi-modality imaging system is described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

While the invention has been described in terms of various specific embodiments, those skilled in the art will recognize that the invention can be practiced with modification within the spirit and scope of the claims.

What is claimed is:

1. A method of examining a patient, the method comprising:
    aligning a patient table with a first examination axis;
    imaging a patient utilizing a first imaging modality while the patient is oriented along the first examination axis;
    sequentially translating a first and a second imaging assembly laterally to align the patient table with a second examination axis, the second examination axis being different than the first examination axis, wherein the first and second examination axes are substantially parallel and sequentially translating the first and second imaging assemblies laterally comprises translating the first and second imaging assemblies generally perpendicularly to the first and second axes; and
    imaging the patient utilizing a second separate imaging modality while the patient is oriented along the second examination axis.

2. A method in accordance with claim 1 further comprising moving the patient table along the first examination axis when imaging the patient utilizing the first imaging modality.

3. A method in accordance with claim 1 wherein imaging a patient utilizing either the first imaging modality or the second imaging modality comprises utilizing at least one of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly.

4. An imaging system comprising:
    at least a first and a second separate imaging assembly for obtaining medical diagnostic images of a patient for at least first and second imaging modalities, said imaging assemblies being aligned along different first and second examination axes;
    a table configured to hold a patient during the first and the second examination; and
    a support mechanism moving said table between a first and a second examination position wherein said table is aligned with said first and second examination axes, respectively, wherein said support mechanism is configured to move said table both rotatably and laterally to align said table with said first and second examination axes, and wherein said support mechanism is configured to move said table laterally in approximately a straight line.

5. An imaging system in accordance with claim 4 wherein said support mechanism comprises a guide member configured to guide said table between said first and second examination axes.

6. An imaging system in accordance with claim 4 further comprising a transport mechanism configured to move at least one of said first and second imaging assemblies between said first and second examination positions.

7. An imaging system in accordance with claim 6 wherein said transport mechanism is configured to move at least one of said first and second imaging assemblies laterally between said first and second examination positions.

8. An imaging system in accordance with claim 4 wherein said first and second examination axes are substantially parallel.

9. An imaging system in accordance with claim 4 wherein said first and second examination axes are substantially parallel, and wherein said support mechanism is configured to move said table generally perpendicularly to said first and second examination axes.

10. An imaging system in accordance with claim 4 wherein said support mechanism comprises a guide member at least a portion of which extends in approximately a straight line.

11. An imaging system in accordance with claim 4 wherein said support mechanism comprises a guide member comprising at least one of a track and a rail.

12. An imaging system in accordance with claim 4 wherein said support mechanism comprises a transport mechanism configured to enable movement of said table in approximately a straight line.

13. An imaging system in accordance with claim 4 wherein said support mechanism comprises a transport mechanism comprising at least one of a caster, a roller, and an air cushion.

14. A method of examining a patient, the method comprising:
    aligning a patient table with a first examination axis;
    imaging a patient utilizing a first imaging modality while the patient is oriented along the first examination axis;
    laterally translating the patient table and at least one of a first and a second imaging assembly to align the patient table with a second examination axis, the second examination axis being different from the first examination axis; and
    imaging the patient utilizing a second separate imaging modality while the patient is oriented along the second examination axis.

15. A method in accordance with claim 14 wherein laterally translating the patient table and at least one of the first and second imaging assemblies comprises simultaneously translating both the patient table and at least one of the first and second imaging assemblies.

16. A method in accordance with claim 14 wherein laterally translating the patient table and at least one of the first and second imaging assemblies comprises simultaneously translating both of the first and second imaging assemblies.

* * * * *